(12) United States Patent
Re (10) Patent No.: US 8,430,884 B2
(45) Date of Patent: Apr. 30, 2013

(54) FEMORAL GUIDE FOR ACL REPAIR HAVING SELECTIVELY DEPLOYABLE FEMORAL SURFACE ENGAGEMENT MEMBER

(75) Inventor: Paul Re, Boston, MA (US)

(73) Assignee: Covidien LP, Mansfield, MA (US)

( * ) Notice: Subject to any disclaimer, the term of this patent is extended or adjusted under 35 U.S.C. 154(b) by 324 days.

(21) Appl. No.: 12/548,856

(22) Filed: Aug. 27, 2009

(65) Prior Publication Data

US 2010/0049203 A1    Feb. 25, 2010

Related U.S. Application Data (63) Continuation-in-part of application No. 12/366,967, filed on Feb. 6, 2009.

(60) Provisional application No. 61/066,575, filed on Feb. 21, 2008.

(51) Int. Cl.
*A61B 17/58* (2006.01)
*A61B 17/60* (2006.01)
*A61F 2/00* (2006.01)

(52) U.S. Cl.
USPC ............................. 606/89; 606/88; 606/86 R (58) Field of Classification Search ............... 606/88, 606/99, 104, 86 R, 89, 96, 167, 170–172
See application file for complete search history.

(56) References Cited

U.S. PATENT DOCUMENTS

| | | | |
|---|---|---|---|
| 4,911,153 A | 3/1990 | Border |
| 5,152,764 A | 10/1992 | Goble |
| 5,250,055 A | 10/1993 | Moore et al. |
| 5,314,429 A | 5/1994 | Goble |
| 5,320,115 A | 6/1994 | Kenna |
| 5,320,626 A | 6/1994 | Schmieding |
| 5,385,567 A | 1/1995 | Goble |
| 5,445,642 A | 8/1995 | McNulty |
| 5,514,144 A | 5/1996 | Bolton |
| 5,520,693 A | 5/1996 | McGuire et al. |
| 5,562,664 A | 10/1996 | Durlacher et al. |
| 5,562,669 A | 10/1996 | McGuire |
| 5,570,706 A | 11/1996 | Howell |
| 5,613,971 A | 3/1997 | Lower et al. |
| 5,891,150 A | 4/1999 | Chan |

(Continued)

FOREIGN PATENT DOCUMENTS

CA    2654486    8/2009
FR    2744621    8/1997

OTHER PUBLICATIONS

PCT International Search Reports dated Oct. 19, 2010 for the corresponding application PCT/US2010/046764, Oct. 25, 2010 for the corresponding application PCT/US2010/046774, Oct. 26, 2010 for the corresponding application PCT/US2010/046769, and Oct. 27, 2010 for the corresponding application PCT/US2010/046804.

*Primary Examiner* — Andrew Yang
*Assistant Examiner* — Olivia C Chang (57) ABSTRACT

A guide for positioning a femoral tunnel during an ACL repair. The device may include a shaft having a distal end and a femoral surface engagement member. The femoral surface engagement member may be selectively deployable relative to the distal end of the shaft. The femoral surface engagement member may have a relatively sharp distal end, that is configured to alter, e.g., pierce, a surface of the femur.

7 Claims, 10 Drawing Sheets

U.S. PATENT DOCUMENTS

| | | |
|---|---|---|
| 5,968,050 A | 10/1999 | Torrie |
| 6,022,356 A | 2/2000 | Noyes et al. |
| 6,254,606 B1 | 7/2001 | Carney et al. |
| 6,309,396 B1 | 10/2001 | Ritland |
| 6,342,057 B1 * | 1/2002 | Brace et al. ............ 606/96 |
| 6,352,538 B2 | 3/2002 | McGuire et al. |
| 6,878,150 B1 | 4/2005 | McGuire et al. |
| 7,025,770 B2 | 4/2006 | McGuire et al. |
| 7,032,599 B2 | 4/2006 | May et al. |
| 7,458,975 B2 | 12/2008 | May et al. |
| 7,491,206 B2 | 2/2009 | Whittaker et al. |
| 2002/0082617 A1 * | 6/2002 | Nishtala et al. ......... 606/139 |
| 2002/0151903 A1 | 10/2002 | Takei et al. |
| 2003/0009173 A1 | 1/2003 | McGuire et al. |
| 2004/0267273 A1 | 12/2004 | Whittaker et al. |
| 2005/0203523 A1 | 9/2005 | Wenstrom et al. |
| 2005/0228399 A1 * | 10/2005 | Kubo et al. ............ 606/96 |
| 2006/0074434 A1 | 4/2006 | Wenstrom, Jr. et al. |
| 2006/0100637 A1 * | 5/2006 | Rathbun et al. ......... 606/96 |
| 2006/0149283 A1 | 7/2006 | May et al. |
| 2006/0293689 A1 | 12/2006 | Miller et al. |
| 2007/0123902 A1 | 5/2007 | Berberich et al. |
| 2007/0191853 A1 | 8/2007 | Stone |
| 2007/0233128 A1 | 10/2007 | Schmieding et al. |
| 2007/0233151 A1 | 10/2007 | Chudik |
| 2008/0103506 A1 | 5/2008 | Volpi et al. |
| 2008/0234819 A1 | 9/2008 | Schmieding et al. |
| 2009/0018654 A1 | 1/2009 | Schmieding et al. |
| 2009/1030417 | 1/2009 | Takahashi |
| 2009/1157081 | 6/2009 | Homan et al. |
| 2009/0187244 A1 | 7/2009 | Dross |
| 2009/0265003 A1 | 10/2009 | Re et al. |

* cited by examiner

FEMORAL GUIDE FOR ACL REPAIR HAVING SELECTIVELY DEPLOYABLE FEMORAL SURFACE ENGAGEMENT MEMBER

CROSS REFERENCE TO RELATED APPLICATIONS

This application is a continuation-in part of, and claims the benefit of priority to, U.S. patent application Ser. No. 12/366,967, filed Feb. 6, 2009, entitled "Guide for Creating a Femoral Tunnel During an ACL Reconstruction," and U.S. Provisional Patent Application Ser. No. 61/066,575, filed Feb. 21, 2008, entitled "Guide for Creating a Femoral Tunnel During an ACL Reconstruction," the disclosures of each being incorporated herein by reference in their entirety. In addition, this application is related to U.S. Provisional Patent Application Ser. No. 61/066,572, filed Feb. 21, 2008, entitled "Device for Orienting the Tibial Tunnel Position During an ACL Reconstruction" and U.S. patent application Ser. No. 12/367,007, filed Feb. 6, 2009, entitled "Device for Orienting the Tibial Tunnel Position During an ACL Reconstruction," the disclosures of each also being incorporated herein by reference in their entirety.

BACKGROUND

1. Technical Field

This invention relates to surgical apparatus and procedures in general, and more particularly to surgical apparatus and procedures for reconstructing a ligament.

2. Background of Related Art

A ligament is a piece of fibrous tissue which connects one bone to another. Ligaments are frequently damaged (e.g., detached or torn or ruptured, etc.) as the result of injury and/or accident. A damaged ligament can cause instability, impede proper motion of a joint and cause pain. Various procedures have been developed to repair or replace a damaged ligament. The specific procedure used depends on the particular ligament which is to be restored and on the extent of the damage.

Figure 1:
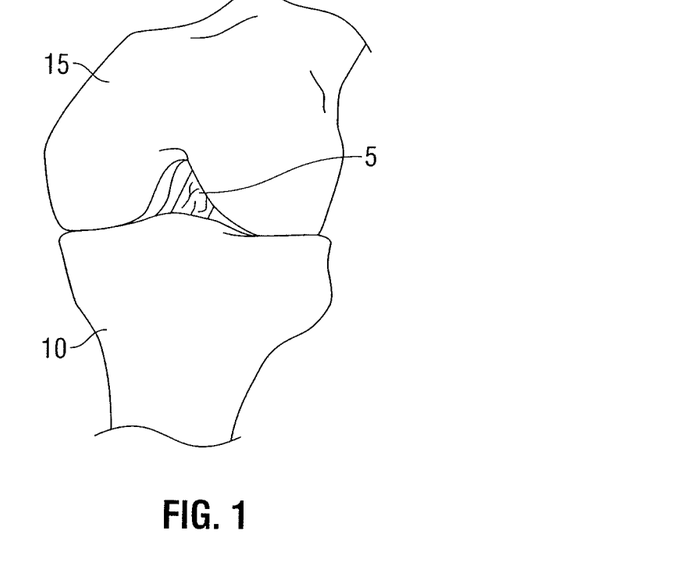
FIG. 1 is a perspective view of a knee joint showing an ACL.
Figure 2:
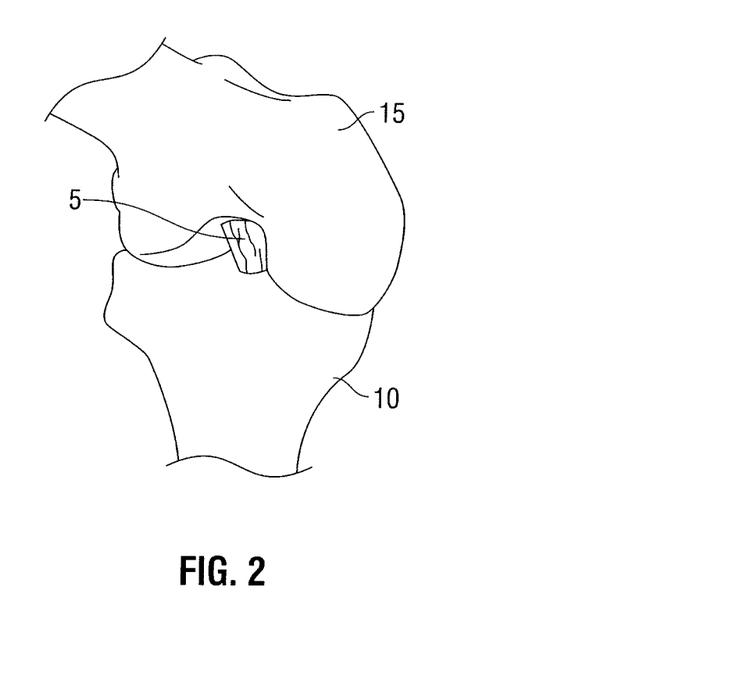
FIG. 2 is an alternate perspective view of the knee joint of FIG. 1.
Figure 3:
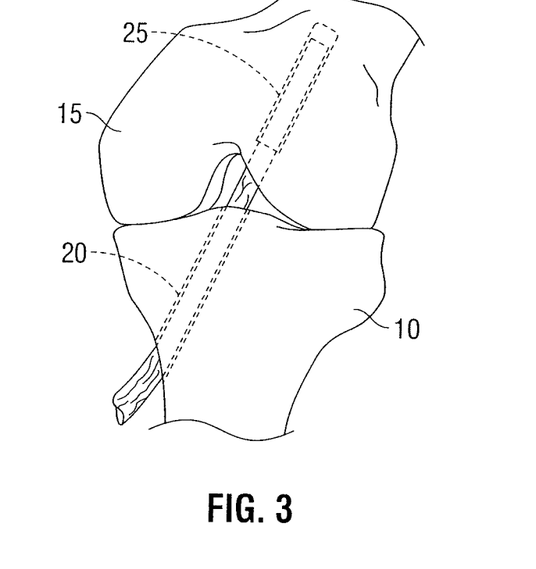
FIG. 3 is a perspective view of a knee joint including tibial and femoral tunnels (shown in phantom) and a ligament graft.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis. For this reason, ACL reconstruction is a common procedure with more than 100,000 cases being performed in the United States annually.

Figure 4:
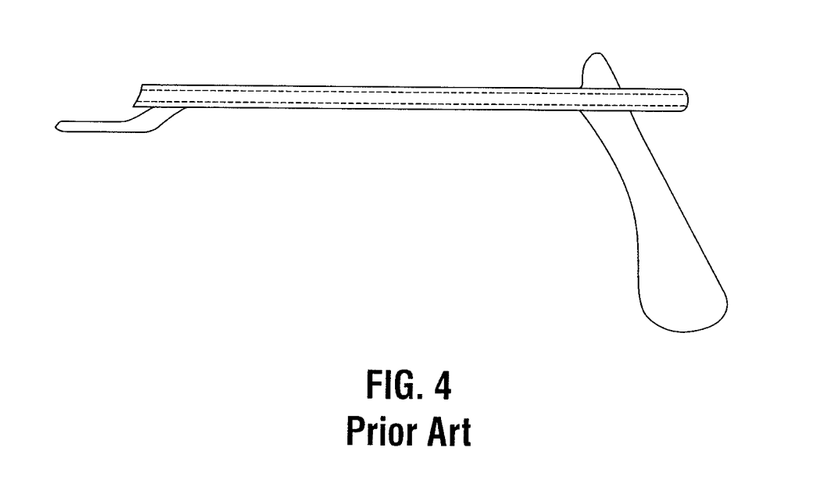
FIG. 4 is a side view of a conventional "over-the-top" femoral guide.
Figure 5:
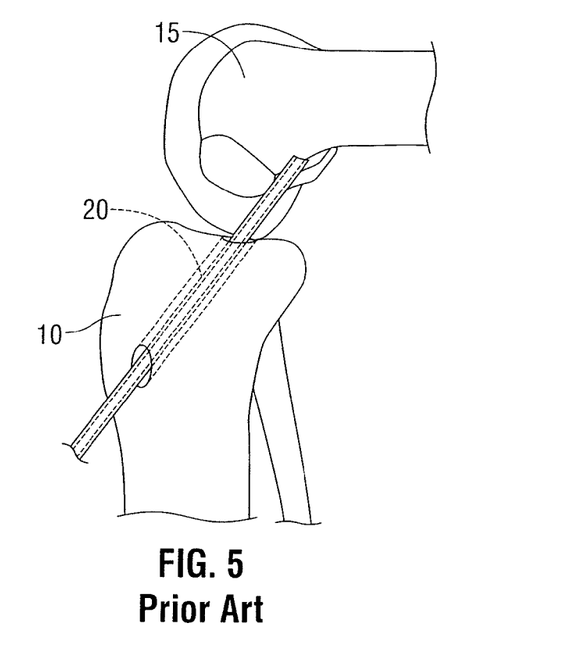
FIG. 5 is side view of a knee joint including the "over-the-top" femoral guide of FIG. 4 accessing the femur using the trans-tibial approach.

Various procedures have been developed to restore and/or reconstruct a damaged ACL through a graft ligament replacement. Traditionally, this procedure is performed utilizing a trans-tibial approach. In this approach, a tibial tunnel or bone tunnel 20 is created in tibia 20 by drilling up through tibia 10. Bone tunnel 20 is then used to access an inner surface of femur 15 to drill a bone tunnel 25 up into femur 15. More particularly, once tibial tunnel 20 is created, a conventional femoral guide, often referred to as an "over-the-top" guide (FIG. 4), is used to accurately locate the femoral tunnel 25. More specifically, the "over-the-top" guide is placed through the tibial tunnel, across the joint, through the femoral notch, and then into position so that the distal finger of the guide is positioned against the backside of the femur. (FIG. 5). Proper placement of the femoral tunnel is imperative in order for the ACL graft to be properly positioned on the femur. However, as a result of using the aforementioned trans-tibial technique and the aforementioned conventional "over-the-top" femoral guide, the position of the femoral tunnel is effectively dictated by the position of the first-drilled tibial tunnel. This often results in a femoral tunnel position, and thus, an ACL reconstruction (i.e., graft orientation, etc.) that is less than optimal.

In an attempt to better position the femoral tunnel, surgeons have recently begun utilizing the so-called "medial portal technique" to drill and create the femoral tunnel. By drilling the femoral tunnel through the medial portal or an accessory portal, the femoral and tibial tunnels may be drilled independently of one another and, therefore, in a more appropriate anatomical position.

Figure 6:
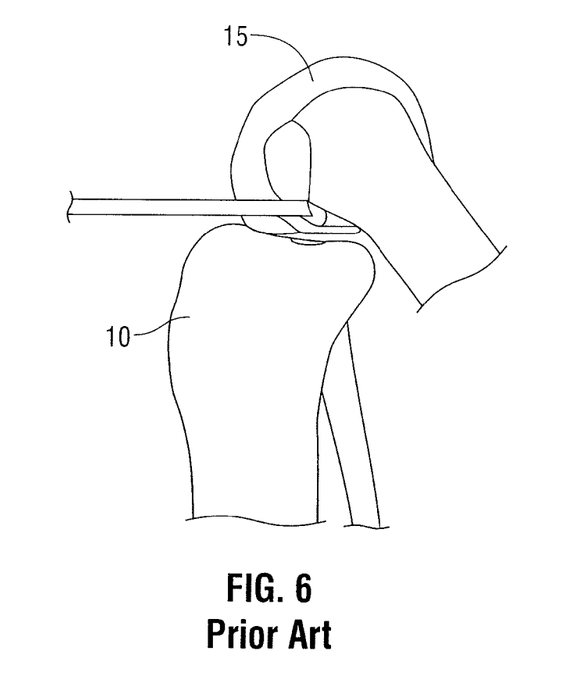
FIG. 6 is a side view of a knee joint including the "over-the-top" femoral guide of FIG. 4 access the femur using the medial portal approach.
Figure 7A:
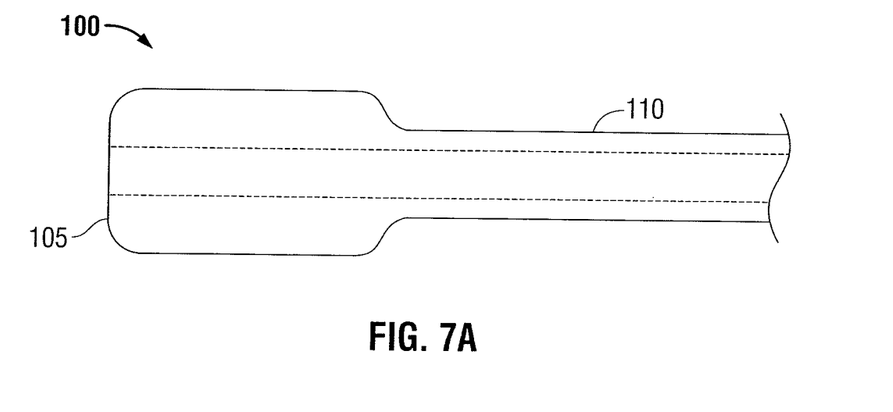
FIGS. 7A-7C are side views of the distal end of various embodiments of a femoral guide according to the present disclosure.
Figure 7B:
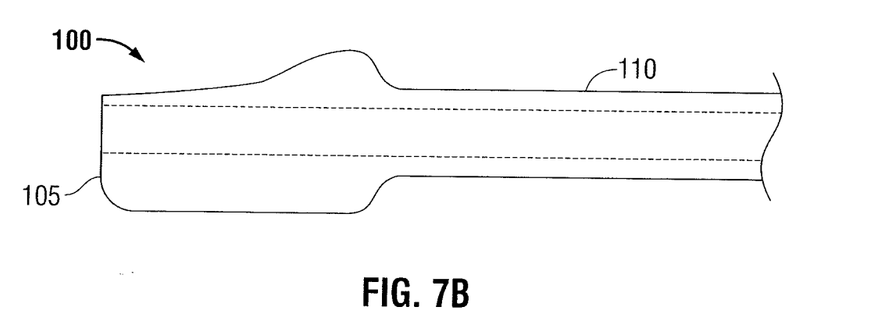
Figure 7C:
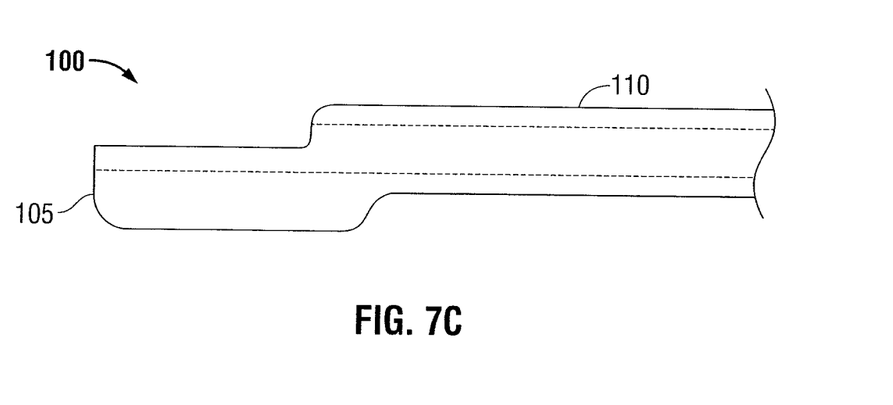
Figure 8A:
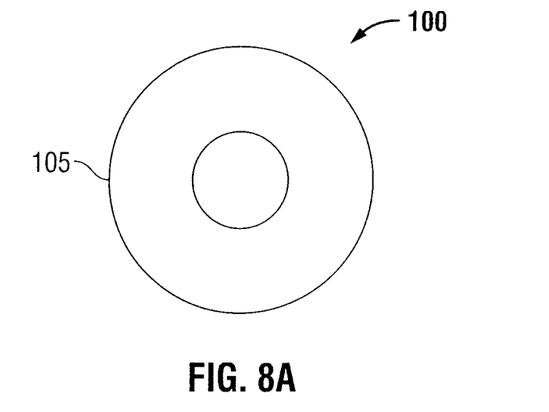
FIGS. 8A-8C are end views of the distal end of the embodiments of FIGS. 7A-7C, respectively.
Figure 8B:
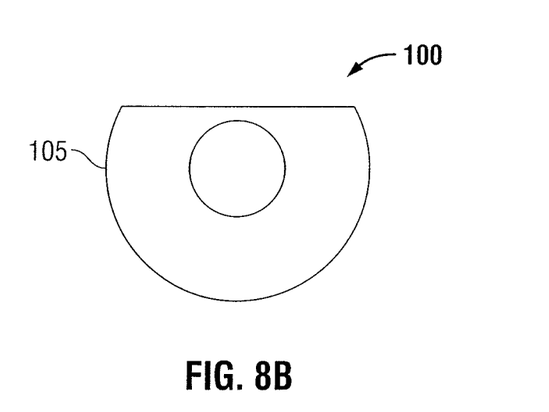
Figure 8C:
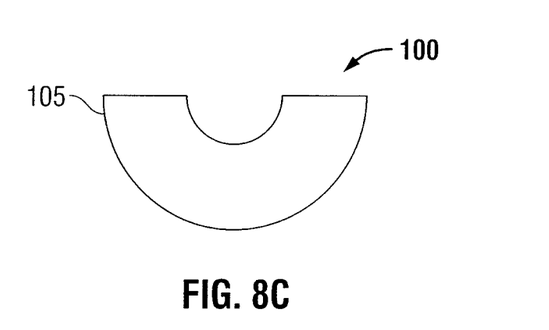
Figure 9A:
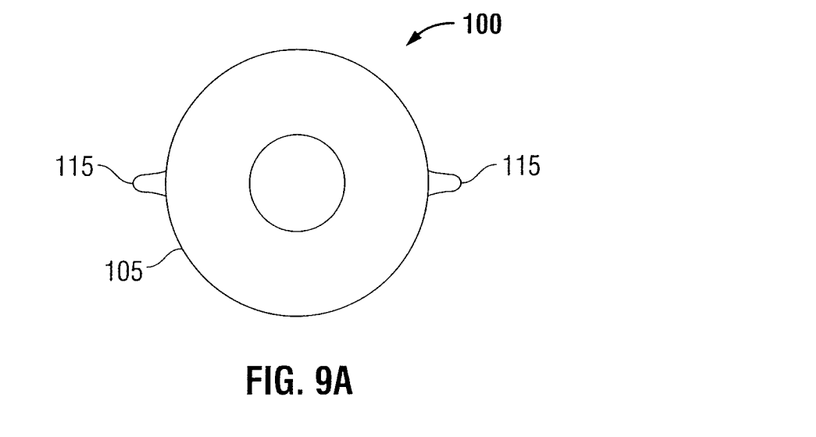
FIGS. 9A-9C are end views of the distal end of alternative embodiments of a femoral guide according to the present disclosure.
Figure 9B:
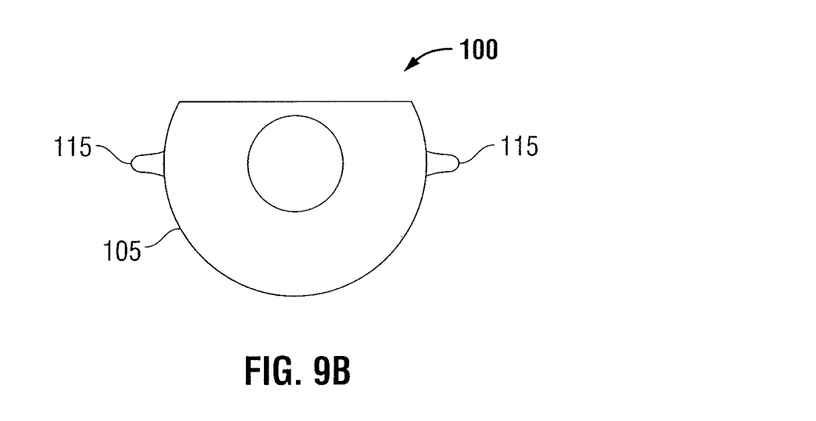
Figure 9C:
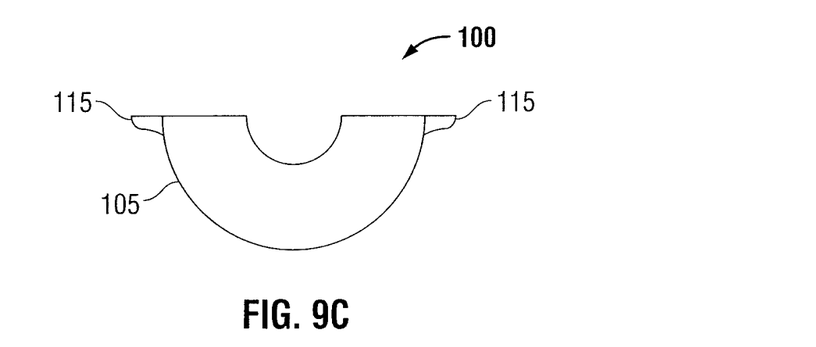
Figure 10A:
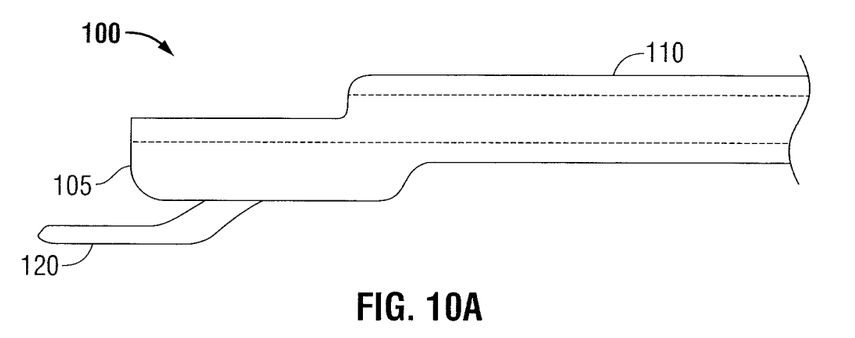
FIG. 10A is a side view of a distal end of a femoral guide according to another embodiment of the present disclosure.
Figure 10B:
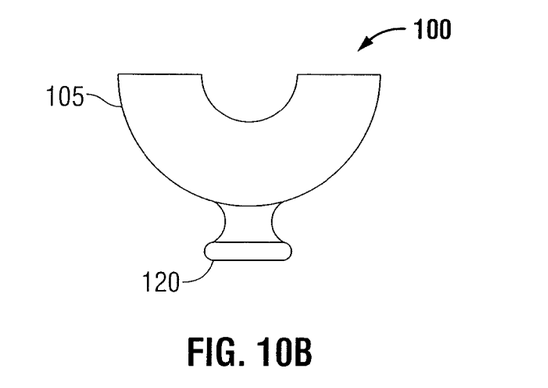
FIG. 10B is an end view of the distal end of the femoral guide of FIG. 10A.
Figure 10C:
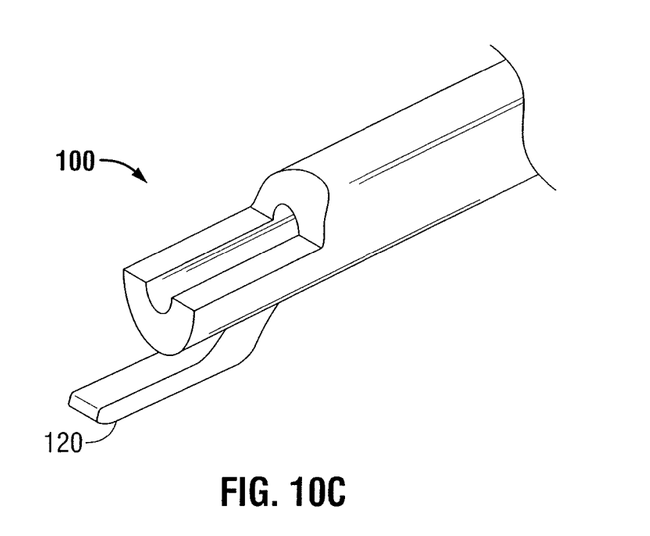
FIG. 10C is a side view of the femoral guide of FIGS. 10A and 10B.
Figure 10D:
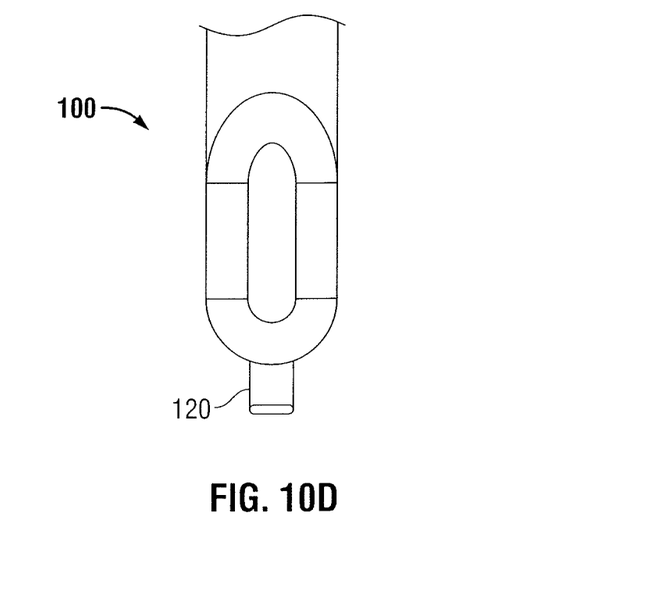
FIG. 10D is an end view of the femoral guide of FIGS. 10A-10C.
Figure 10E:
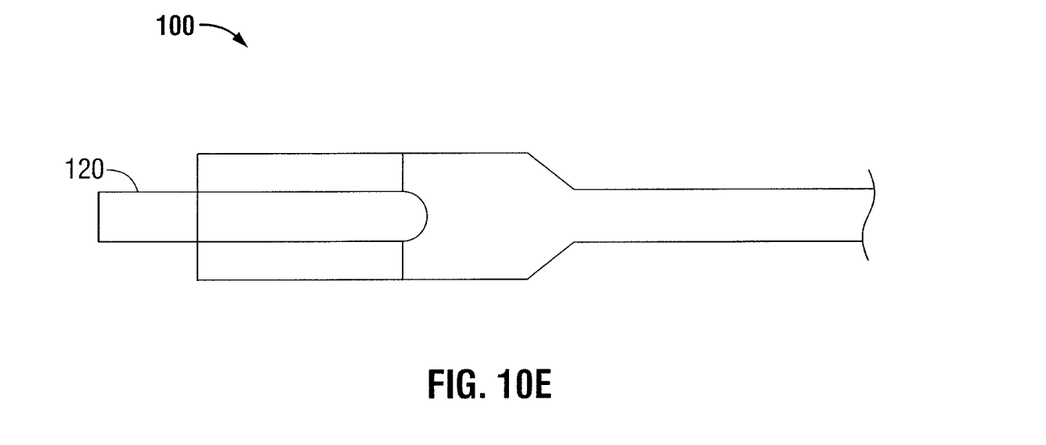
FIG. 10E is top view of the distal end of the femoral guide of FIGS. 10A-10D.

As shown in FIG. 6, when drilling the femoral tunnel through the medial portal, surgeons typically still use the same "over-the-top" femoral guide used during the aforementioned trans-tibial approach. However, because the "over-the-top" femoral guide is designed for use in a trans-tibial approach, the "over-the-top" femoral guide is not ideal for use in a medial portal approach. These "over-the-top" femoral guides generally have narrow-shaped distal tip geometries to aid in their ability to pass through the tibial tunnel. In addition, such femoral guides have an offset spatula design to hook the posterior femoral notch, thereby aiding in positioning of the guide. Aside from this spatula design, these femoral guides have no other specific referencing geometries for properly positioning the femoral tunnel.

Traditionally, surgeons utilize what is known as a "clock face" orientation in order to decide where to place the femoral tunnel within the notch of knee. This clock face orientation technique designates positions along the notch from 9 o'clock to 3 o'clock, depending on which knee is being reconstructed. This technique, while seemingly simplistic, is limited by a number of factors, one being that the positioning of the imaginary clock face along the notch is completely subjective and hence widely affected by the specific implementation of the surgeon. Therefore, it would be beneficial to have a femoral guide for use in medial approach ACL reconstruction surgery that is configured for more accurate femoral tunnel positioning. In addition, it would be beneficial if the femoral guide is designed in such a way that it might also be utilized during a trans-tibial approach.

SUMMARY

A guide for positioning a guide wire on a femur to allow a tunnel to be formed in the femur along the guide wire is provided. The guide includes an elongated shaft having proximal and distal ends, and a distal tip formed on the distal end of the elongated shaft, the distal tip having a diameter substantially similar in size to the diameter of the desired resultant femoral tunnel, wherein the elongated shaft and the distal tip are cannulated to receive the guide wire.

The distal tip further may further include at least one of opposed fingers and a distal projection. The opposed fingers or distal projection may be configured to reference a leading edge of the posterior cruciate ligament. The opposed fingers or distal projections may further be configured to reference a posterior femoral cortex. The elongated shaft may be configured to extend across a knee joint, the length of a tibial tunnel, or out of a medial port. The distal end may include a substantially circular cross-section, a substantial semi-spherical cross-section, or an unroofed cross-section.

Additionally, there is provided a method of positioning a femoral tunnel during an ACL reconstruction. The method includes the steps of providing a femoral guide including an elongated shaft having a distal end, the distal end including a diameter substantially similar in size to the diameter of the desired resultant femoral tunnel, wherein the elongated shaft and the distal end are cannulated to receive a guide wire therethrough, inserting the femoral guide into a knee joint, positioning the distal end of the guide against the femur, and inserting the guide wire through the femoral guide and into the femur.

The femoral guide may include one of opposed fingers and a distal projection configured for referencing a posterior cruciate ligament. The method may further include the step of referencing a leading edge of a posterior cruciate ligament and/or the posterior femoral cortex. The method may also include the step of flexing the knee to 120 degrees. The femoral guide may be inserted into the knee joint using a medial portal approach or a trans-tibial approach.

In accordance with various embodiments, the present invention may provide a device for positioning a femoral tunnel during ACL reconstruction, the device comprising: a shaft having a distal end; and a femoral surface engagement member, the femoral surface engagement member being selectively deployable relative to the distal end of the shaft. The femoral surface engagement member may be longitudinally moveable relative to shaft. The femoral surface engagement member may be moveable relative to the shaft between a first position, in which the distal end of the femoral surface engagement member is enclosed by the distal end of the shaft, and a second position, in which the distal end of the femoral surface engagement member extends distally beyond the distal end of the shaft. The femoral surface engagement member may have a relatively sharp distal end that is configured to alter, e.g., pierce, a surface of the femur. The device may also include an actuating member for moving the shaft and the femoral surface engagement member relative to each other. The shaft may define a lumen that is configured to receive a guide wire therethrough.

In accordance with various embodiments, the present invention may also provide a device for positioning a femoral tunnel during ACL reconstruction, the device comprising: a shaft having a distal end; and a femoral surface engagement member, the femoral surface engagement member having a relatively sharp distal end that is configured to alter a surface of the femur. The relatively sharp distal end may be configured to alter a surface of the femur by one of penetrating, gouging and piercing the surface of the femur. The femoral surface engagement member may be selectively deployable relative to the distal end of the shaft. The femoral surface engagement member may be longitudinally moveable relative to shaft. The femoral surface engagement member may be moveable relative to the shaft between a first position, in which the distal end of the femoral surface engagement member is enclosed by the distal end of the shaft, and a second position, in which the distal end of the femoral surface engagement member extends distally beyond the distal end of the shaft. The device may also include an actuating member for moving the shaft and the femoral surface engagement member relative to each other. The shaft may define a lumen that is configured to receive a guide wire therethrough.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION OF THE EMBODIMENTS

The femoral guide of the present disclosure is designed to be used in determining the position of a femoral tunnel guide wire which facilitates the positioning of a femoral tunnel during an ACL reconstruction. As with conventional femoral guides, the femoral guide of the present disclosure may reference an "over-the-top" position with an offset spatula; however, it can also be designed and utilized without such an offset spatula. This includes having no spatula, or instead having one or multiple spike projections or other similar projections to hold the spatula in position on the bone.

FIGS. 7A-10E show various embodiments of a femoral guide 100 formed in accordance with the present disclosure. Femoral guide 100 generally includes a distal tip 105 and a shaft 110 extending proximally therefrom. Distal tip 105 of femoral guide 100 may be dimensioned and configured to have the same geometry and circumference as the desired resulting femoral tunnel. In this manner, distal tip 105 acts as a visual aid to assist the surgeon in determining proper tunnel placement by providing a direct visual confirmation of where the resulting femoral tunnel will be located. Alternatively, distal tip 105 may be formed with a semi-hemispherical cross-section (FIGS. 7B, 8B and 9B), or with an "unroofed" cross-section (FIGS. 7C, 8C, 9C and 10A-E) to aid in visualization.

Shaft 110 of femoral guide 100 is configured to be of such a length so as to at least extend (i) across the knee joint, (ii) across the length of the tibial tunnel and/or (iii) out of the medial portal. Shaft 110 and distal tip 105 are cannulated so as to accept (and thereby aim) a guidewire of an appropriate circumference, length and width.

In addition, the geometry of distal end 105 of femoral guide 100 may include (i) diametrically-opposed fingers 115 (FIGS. 9A-9C), and/or (ii) a distal projection 120 (FIGS. 10A-10E). Fingers 115 and/or projection 120 serve to reference the leading edge of the posterior cruciate ligament (PCL) and the posterior femoral cortex. Using the PCL as an anatomical reference enables a surgeon to set the femoral guide wire, and therefore the resulting femoral tunnel, in a position that better avoids any impingement of the PCL after the graft ligament has been placed in position. Such ACL/PCL impingement occurs when the femoral tunnel has been improperly positioned. In this manner, femoral guide 100 is configured to avoid any such ACL/PCL impingement, by using the PCL as an anatomical reference during formation of the femoral tunnel.

Figure 11:
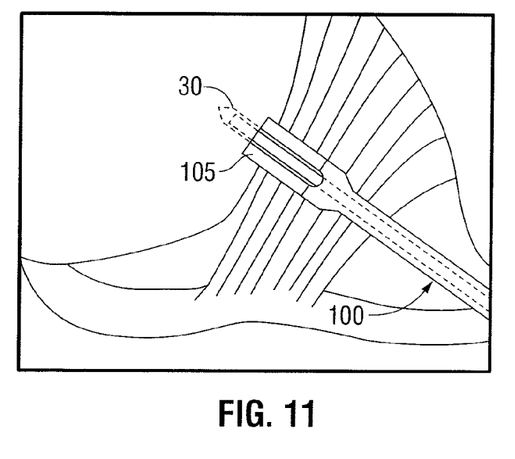
FIG. 11 is a partial cut-away view of a femoral guide according to an embodiment of the present disclosure being used in a medial portal approach.
Figure 12:
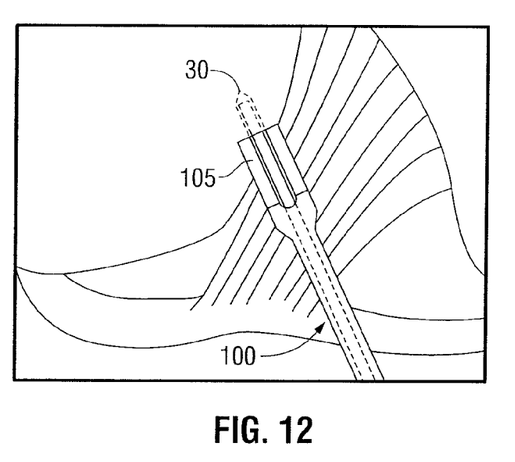
FIG. 12 is a partial cut-away view of a femoral guide according to an embodiment of the present disclosure being used in a trans-tibial approach.

As shown in FIG. 11, femoral guide 100 may be used in a medial portal approach with the knee in hyper-flexion, at approximately 120 degrees. However, it should be appreciated that femoral guide 100 may also be used with any ACL reconstruction approach, and with any angle of knee flexion. See, for example, FIG. 12, where femoral guide 100 is used during a traditional trans-tibial approach. Because of the size and/or configuration of distal end 105 of femoral guide 100, for use in the trans-tibial approach, femoral guide 100 may be halved, with one half for use with the right knee and the other half for use with the left knee.

Once the location of femoral tunnel 25 is identified by the surgeon with distal end 105 of femoral guide 100, guide wire 30 (FIG. 11) is extended through the cannulated shaft of elongated shaft 110 and into femur 15. Once guide wires 30 has been inserted into femur 15 to a desired depth, femoral guide 100 is then removed from about guide wire 30 and from the medial portal into the knee. A cannulated drill bit (not shown) is then received about guide wire 30 and through the medial portal to drill femoral tunnel 25.

Figure 13:
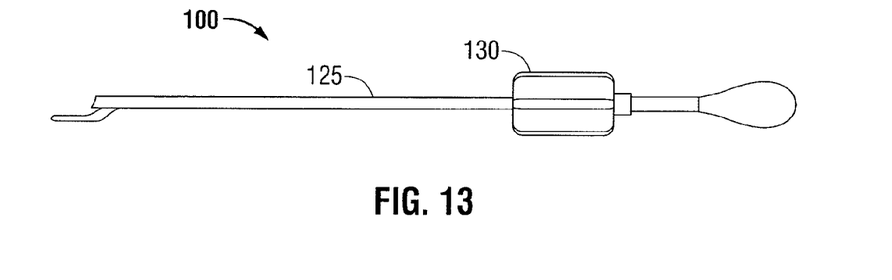
FIG. 13 is a side view of the proximal end of a femoral guide according to an embodiment of the present disclosure.

Looking next at FIG. 13, the proximal (or "butt") end 125 of femoral guide 100 is preferably provided with a docking port 130 to mate with a handle 135 to aid the surgeon in aiming the guide more easily and accurately. Handle 135 may be configured in any desired geometry so as to be ergonomically comfortable and/or to facilitate in the placement or holding of distal tip 105 in a particular position.

Femoral guide 100 provides surgeons with several significant improvements over prior art femoral guides. First, the distal portion of femoral guide 100 is configured (both in shape and diameter), to mirror that of the resulting tunnel and, therefore, the resulting graft. This gives the surgeon a visual "preview" or reference of the femoral tunnel prior to actually drilling the femoral tunnel. In addition, the distal shape of the femoral guide references the leading edge of the PCL's insertion onto the femur (i.e., the location where the PCL attaches to the femur) and places the resulting femoral tunnel in a position which avoids graft ACL/PCL impingement.

Some of the particular embodiments shown hereinabove illustrate the use of a femoral surface engagement member which may be employed, as described hereinabove, by being brought into contact against a surface of the femur by a surgeon. For such embodiments, the femoral surface engagement member 210 may have a generally flat upper surface when viewed in cross-section. In addition, the femoral surface engagement member 210 may have a straight or rounded distal end such that contact thereby with a surface of the femur does not alter the surface of the femur. It should be recognized that the present invention may also include other embodiments in which the femoral surface engagement member has a different shape, and functions differently from, the distal offset projection described hereinabove. For example, the femoral surface engagement member 210 may include a relatively sharp point at its distal end that is configured to alter, e.g., penetrate, gouge or otherwise pierce, the surface of the femur. In this manner, a surgeon may choose to use the femoral surface engagement member 210 in the same manner as described hereinabove, e.g., whereby the surgeon determines a position of a femoral tunnel by resting an upper surface of the femoral surface engagement member 210 against a surface of the femur, e.g., the posterior femoral notch, by a surgeon, and/or the surgeon may choose to use the femoral surface engagement member 210 in the manner that is different from that described hereinabove. For example, the surgeon may use the relatively sharp end of the femoral surface engagement member 210 to reference an anatomical feature of the femur so as to help determine a position of a femoral tunnel, and then may push the relatively sharp end of the femoral surface engagement member 210 into the surface of the femur, so as to help maintain the femoral surface engagement member 210 in the determined position relative to the femur during at least a portion of the surgical procedure.

Figure 14:
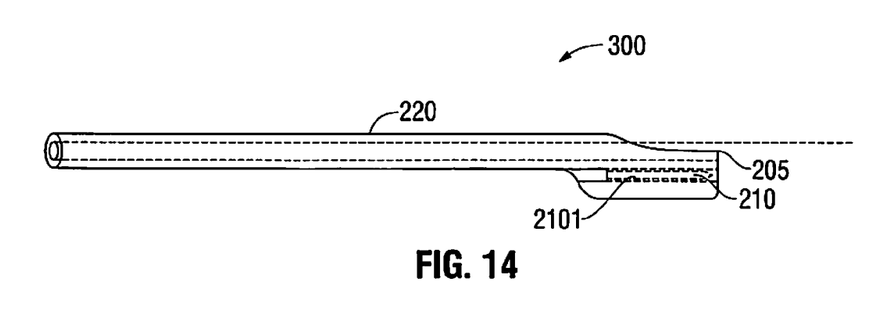
FIG. 14 is a side view of a femoral tunnel positioning guide in a first position, according to an example embodiment of the present invention.
Figure 15:
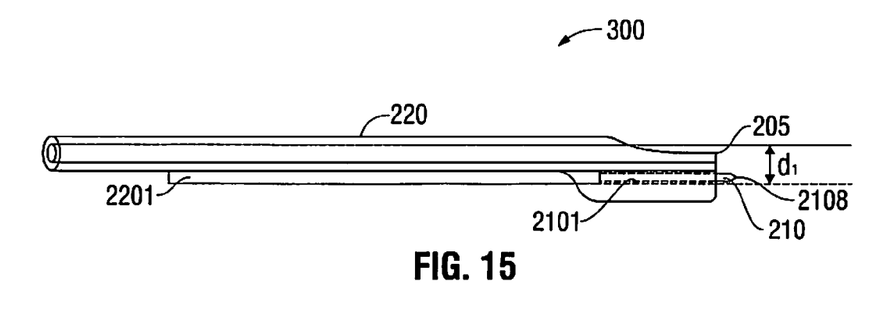
FIG. 15 is a side view of the femoral tunnel positioning guide shown in FIG. 14 in a second position.
Figure 16:
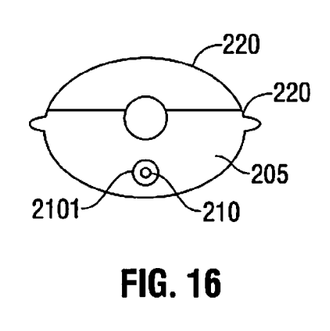
FIG. 16 is a front view of the distal portion of the femoral tunnel positioning guide shown in FIG. 14.

Furthermore, while some of the particular embodiments shown hereinabove have the femoral surface engagement member 210 being permanently deployed relative to the cannulated body 220, it should be recognized that the present invention may also include other embodiments in which the femoral surface engagement member 210 is not permanently deployed relative to the cannulated body 220. For example, various embodiments of the present invention may include an arrangement in which the cannulated shaft 220 and the femoral surface engagement member 210 are separate components whereby the femoral surface engagement member 210 may be selectively deployed by a user relative to the cannulated body 220. FIGS. 14, 15 and 16 illustrate an example embodiment of a femoral tunnel positioning device 300 having an arrangement in which the femoral surface engagement member 210 may be selectively deployed by a user relative to the cannulated body 220. Specifically, FIGS. 14, 15 and 16 illustrate an example embodiment of the present invention having an arrangement in which the femoral surface engagement member 210 is selectively and longitudinally deployable by a user relative to a distal end 205 of the cannulated body 220 via a second lumen 2101. The second lumen 2101 extends through at least a portion of the cannulated shaft 220 and communicates with the distal end 205 of the cannulated shaft 220.

Providing an arrangement in which the femoral surface engagement member 210 may be selectively deployed by a user relative to the cannulated body 220 may provide additional advantages as compared to embodiments in which the femoral surface engagement member 210 is permanently deployed relative to the cannulated body 220. For example, and as described hereinabove, in embodiments in which the femoral surface engagement member 210 is permanently deployed relative to the cannulated body 220, a distal end 2108 of the femoral surface engagement member 210 is typically disposed at a fixed longitudinal distance relative to the distal end 205 of the cannulated shaft 220. This longitudinal distance is reflective of the function of the femoral surface engagement member 210 in combination with, e.g., the position of the cannulated shaft 220 relative to the medial portal. More specifically, this longitudinal distance reflects that, when the device is in place within a patient such that the cannulated shaft 220 is disposed within the medial portal formed by the surgeon (or is disposed within the tibial tunnel in the event that the surgeon has employed the trans-tibial technique described hereinabove), the femoral surface engagement member 210 advantageously is configured to position the longitudinal axis of the lumen of the shaft 220 into alignment with a desired location of a femoral tunnel when the distal end 205 is in contact with a first surface of the femur and when the femoral surface engagement member 210 is in contact with a second surface, e.g., the posterior femoral notch, of the femur. Although having an arrangement in which the femoral surface engagement member 210 is permanently deployed relative to the cannulated body 220 may provide the advantage of insuring that the femoral surface engagement member 210 is long enough to remain in contact with the second surface of the femur once the device is already in position within the patient's knee, it may have the disadvantage of making it more difficult for the surgeon to initially insert the device into the patient's knee and to get the device into the desired position once inserted. This potential difficulty may manifest itself due to a surgeon's general desire to have a medial portal which is as small as possible (e.g., to promote faster healing and less pain), in combination with the fact that the anatomical structures of the knee joint may result in a relatively crowded internal surgical space. Given these anatomical constraints, when a femoral surface engagement member 210 is permanently deployed relative to the cannulated shaft such that the distal end of the femoral surface engagement member extends a relatively large distance beyond the distal end of the cannulated shaft, the surgeon may have difficulty fitting the device through a medial portal and manipulating the device once in the internal surgical space.

In addition, having an arrangement in which the femoral surface engagement member is permanently deployed relative to the cannulated body prevents the surgeon from adjusting the longitudinal distance to accommodate variations in different patients' anatomy, e.g., a larger longitudinal distance may be desirable for many different reasons, such as for a large patient, for a patient that has atypical PCL attachment sites, etc. Still further, in those embodiments in which the distal end of the femoral surface engagement member is relatively sharp, having an arrangement in which the femoral surface engagement member is permanently deployed relative to the cannulated body may cause the relatively sharp end to be permanently exposed during the entire surgical procedure, which may increase the likelihood of inadvertent damage being caused thereby to the internal anatomy of the knee, particularly when the surgeon is trying to insert the femoral tunnel positioning device and get it into position.

Providing an arrangement in which the femoral surface engagement member 210 may be selectively deployed by a user relative to the cannulated body 220 may overcome some of these difficulties. For example, in embodiments in which the femoral surface engagement member 210 may be selectively deployed by a user relative to the cannulated body 220, the cannulated shaft 220 and the femoral surface engagement member 210 may be moveable between various positions to facilitate their insertion and/or positioning during the surgical procedure. Referring to the example embodiment illustrated in FIGS. 14, 15 and 16, there is shown an arrangement in which the insertion and/or positioning of the device during the surgical procedure may be facilitated by having the femoral surface engagement member 210 be selectively deployed by a user relative to the cannulated body 220. Referring to FIG. 14, the femoral tunnel positioning device 300 is shown in a first position, e.g., in which the femoral surface engagement member 210 is in a first, e.g., retracted, position relative to the cannulated shaft 220. In the embodiment shown, in this first position, the distal end 2108 of the femoral surface engagement member 210 is located proximally relative to the distal end 205 of the cannulated shaft 220 so as to be totally enclosed by the cannulated shaft 220, thereby shortening the overall length of the femoral tunnel positioning device 300. This relatively short overall length may help enable a surgeon to more easily insert the device 300 into the medial portal and to place the device into an advantageous position prior to its final positioning. Once the surgeon has inserted the device 300 through the medial portal and placed the device into a generally desired position, the surgeon may then cause the device 300 to move to a second position, such as the position illustrated in FIG. 15. As shown in FIG. 15, in the second position, the femoral surface engagement member 210 is moved longitudinally relative to the cannulated shaft 220 (it should be recognized that, additionally or alternatively, the femoral surface engagement member 210 may be moved or selectively deployed in a manner other than longitudinally relative to the cannulated shaft 220, e.g., pivotably, rotatably, etc.). This longitudinal movement causes the distal end 2108 of the femoral surface engagement member 210 to extend distally beyond the distal end 205 of the cannulated shaft 220, thereby increasing the overall length of the femoral tunnel positioning device 300. The amount of longitudinal movement may be any distance. Once deployed, the femoral surface engagement member 210 may then be used in any of the manners described hereinabove, e.g., to contact the posterior femoral notch, to alter such as piercing a femoral surface, etc. By enabling a surgeon to selectively shorten and lengthen the overall length of the distal end of the femoral tunnel positioning device 300 after the device 300 is already inserted into the medial portal and after the device has already been placed into an advantageous position, the surgeon may have relatively less difficulty fitting the shortened device through the medial portal, and then manipulating the device into a desirable position while in the integral surgical space.

In addition, having an arrangement in which the femoral surface engagement member 210 may be selectively deployed by a user relative to the cannulated body 220 may enable a surgeon to adjust the longitudinal position of the femoral surface engagement member 210 relative to the cannulated body 220 in order to accommodate variations in different patients' anatomy. Still further, in those embodiments in which the distal end 2108 of the femoral surface engagement member 210 is relatively sharp, having an arrangement in which the femoral surface engagement member 210 may be selectively deployed by a user relative to the cannulated body 220 may improve the safety of the device. Referring to FIG. 14, the femoral tunnel positioning device 300 is shown in a first, e.g., retracted, position, in which the relatively sharp distal end 2108 of the femoral surface engagement member 210 is located proximally relative to, and is totally enclosed by, the distal end 205 of the cannulated shaft 220. Enclosing the relatively sharp distal end 2108 of the femoral surface engagement member 210 within the distal end 205 of the cannulated shaft 220 may help a surgeon to more safely insert the device 300 into the medial portal and to place the device into an advantageous position prior to its final positioning.

Once the surgeon has inserted the device 300 through the medial portal and placed the device into a generally desired position, the surgeon may then cause the device 300 to move to the second, e.g., extended, position, such as the position illustrated in FIG. 15 in which longitudinal movement of the femoral surface engagement member 210 relative to the cannulated shaft 220 causes the distal end 2108 of the femoral surface engagement member 210 to extend distally beyond the distal end 205 of the cannulated shaft 220. Once deployed, the femoral surface engagement member 210 may then be used in any of the manners described hereinabove. By enabling a surgeon to selectively deploy the relatively sharp distal end 2108 of the femoral surface engagement member 210 from within the distal end 205 of the cannulated shaft 220 until after the device 300 is already inserted into the medial portal and after the device has already been placed into an advantageous position, there may be a decreased likelihood of inadvertent damage being caused by the femoral surface engagement member 210 to the internal anatomy of the knee.

As set forth above, once the surgeon has inserted the device 300 through the medial portal and placed the device into a generally desired position, the surgeon may then cause the device 300 to move to a second position, such as the position illustrated in FIG. 15. There are various ways in which the surgeon may cause the device to move between the first and second positions. For example, the femoral tunnel positioning device 300 may include structural features that enable a surgeon to move the device 300 between the first and second positions. In such an arrangement, an actuating member 2201, as shown schematically in FIG. 15, may extend along at least a portion of the cannulated shaft 220, e.g., either externally of the cannulated shaft 220 or internally within a lumen of the cannulated shaft 220. A distal end of the actuating member 2201 may engage a portion of the femoral surface engagement member 210. A proximal end of the actuating member 2201 may be accessible to a surgeon when the device 300 is positioned within a patient's body. In this manner, when the device 300 is positioned within a patient's body, e.g., after the surgeon has preliminarily positioned the device 300 within the surgical space, the surgeon may manipulate the proximal end of the actuating member 2201, thereby causing the distal end of the actuating member 2201 to engage the femoral surface engagement member 210 and move the femoral surface engagement member 210 from its first position to its second position. It should be recognized that the actuating member 2201 shown in FIG. 15 is merely one of many types of actuating members 2201 that may be employed for the purpose of moving the device 300, and specifically the femoral surface engagement member 210, between first and second positions.

It should be understood that many additional changes in the details, materials, steps and arrangements of parts, which have been herein described and illustrated in order to explain the nature of the present disclosure, may be made by those skilled in the art while still remaining within the principles and scope of the disclosure.

What is claimed is:

1. A device for positioning a femoral tunnel during ACL reconstruction, the device comprising:
    a shaft having a distal end and defining a longitudinal axis, the distal end of the shaft defining a hemispherical cross-section to aid in visualization; and
    a femoral surface engagement member supported by the shaft parallel to and laterally spaced from the longitudinal axis, the femoral surface engagement member being selectively deployable relative to the distal end of the shaft between a retracted state wherein a distal end of the femoral surface engagement member is disposed proximally of the distal end of the shaft and a deployed state wherein the distal end of the femoral surface engagement member extends distally of the distal end of the shaft.

2. The device of claim 1, wherein the femoral surface engagement member is longitudinally moveable relative to shaft.

3. The device of claim 1, wherein the femoral surface engagement member is moveable relative to the shaft between a first position, in which the distal end of the femoral surface engagement member is enclosed by the distal end of the shaft, and a second position, in which the distal end of the femoral surface engagement member extends distally beyond the distal end of the shaft.

4. The device of claim 1, wherein the femoral surface engagement member has a relatively sharp distal end.

5. The device of claim 4, the relatively sharp distal end of the femoral surface engagement member is configured to alter a surface of the femur.

6. The device of claim 1, further comprising an actuating member for moving the shaft and the femoral surface engagement member relative to each other.

7. The device of claim 1, wherein the shaft defines a lumen that is configured to receive a guide wire therethrough.

* * * * *